(12) United States Patent
Tenten et al.

(10) Patent No.: US 6,252,122 B1
(45) Date of Patent: Jun. 26, 2001

(54) INDUSTRIAL PROCESS FOR THE HETEROGENEOUSLY CATALYTIC GAS-PHASE OXIDATION OF PROPANE TO FORM ACROLEIN

(75) Inventors: Andreas Tenten, Maikammer; Theo Proll, Bad Dürkheim; Hans-Peter Schildberg, Neustadt, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/147,340

(22) PCT Filed: May 28, 1997

(86) PCT No.: PCT/EP97/02762

§ 371 Date: Dec. 4, 1998

§ 102(e) Date: Dec. 4, 1998

(87) PCT Pub. No.: WO97/46506

PCT Pub. Date: Dec. 11, 1997

(30) Foreign Application Priority Data

Jun. 4, 1996 (DE) .............................. 196 22 331

(51) Int. Cl.$^7$ .......................... C07C 45/33; C07C 51/16; C07C 51/23; B01J 23/00
(52) U.S. Cl. ...................... 568/475; 568/469.9; 562/532; 562/535; 562/549; 502/244; 502/312
(58) Field of Search .................................... 562/532, 535, 562/549; 502/312, 244; 568/399, 475, 469.9, 470

(56) References Cited

U.S. PATENT DOCUMENTS

| | | | |
|---|---|---|---|
| 3,147,084 | 9/1964 | Franzen et al. | 23/288 |
| 3,775,474 | 11/1973 | Ohara et al. | 46/27.203 |
| 3,893,951 | 7/1975 | Grasselli et al. | 252/468 |
| 3,954,855 | 5/1976 | Wada et al. | 260/530 N |
| 4,066,704 | * 1/1978 | Harris et al. | 260/604 R |
| 4,302,610 | 11/1981 | Conner et al. | 568/425 |
| 4,339,355 | 7/1982 | Decker et al. | 252/464 |
| 4,472,314 | 9/1984 | Conner et al. | 260/413 |

FOREIGN PATENT DOCUMENTS

| | | |
|---|---|---|
| 1105352 | 7/1995 | (CN) . |
| 20 58 054 | 6/1971 | (DE) . |
| 2 201 528 | 11/1972 | (DE) . |
| 26 26 887 A1 | 12/1977 | (DE) . |
| 28 30 765 A1 | 1/1980 | (DE) . |
| 29 09 671 A1 | 10/1980 | (DE) . |
| 31 51 805 C2 | 7/1983 | (DE) . |
| 43 02 991 A1 | 8/1994 | (DE) . |
| 44 31 949 A1 | 3/1995 | (DE) . |
| 0 010 902 A1 | 5/1980 | (EP) . |
| 0 117 146 A1 | 8/1984 | (EP) . |
| 0 293 859 A1 | 12/1988 | (EP) . |
| 0 427 508 A1 | 5/1991 | (EP) . |
| 0 609 122 A1 | 8/1994 | (EP) . |
| 02 083 348 | 3/1990 | (JP) . |
| 176878 | 12/1965 | (RU) . |

OTHER PUBLICATIONS

"New Horizons in Catalysis" Tokyo, Jun.–Jul., 1980, "Propane Oxidation Over Mixed Metal Oxides: Perovskites, Trirutiles and Columbites", Wm. Curtis Conner, Jr. (pp. 1224–1238).

Studies in Surface Science and Catalysis 82, 1994, "Selective Oxidation of Propane in the Presence of Bismuth–Based Catalysts", J.Barrault,et al. (pp. 305–314).

Studies in Surface Science and Catalysis 82, 1994 "Oxidation and Ammoxidation of Propane over Tetragonal Tupe $M_5+OPO_4$ Catalysts",Matsuura, et al. (pp. 271–279).

Russian Original Document 176878 (published in 1966), A.N. Schatalowa,et al. In Neftechemi ja 8 ( 1968) (pp. 365–369).

Catalysis Today, 13, 1992 "Catalytic (amm)oxidation of Propane with Molecular Oxygen Over Complex Metal Oxides: Involvement of Homogeneous Reaction in Gas Phase" Y.C Kim, et al. (pp. 673–678).

* cited by examiner

Primary Examiner—Sreeni Padmanabhan
(74) Attorney, Agent, or Firm—Oblon, Spivak, McClelland, Maier & Neustadt, PC

(57) ABSTRACT

In an industrial process for the heterogeneously catalyzed gas-phase oxidation of propane with molecular oxygen to give acrolein, the feed gas mixture having an initial undiluted molar ratio of the reactants propane:$O_2$ of 7:3 is diluted with the reactant propane and, if desired, inert gases in such a way that the feed gas mixture comprises more than 70% by volume of propane and at least 5% by volume of $O_2$.

82 Claims, No Drawings

INDUSTRIAL PROCESS FOR THE HETEROGENEOUSLY CATALYTIC GAS-PHASE OXIDATION OF PROPANE TO FORM ACROLEIN

This is the U.S. National Stage Application of PCT/EP97/02762 filed May 28, 1997.

The present invention relates to a novel process for the industrial heterogeneously catalyzed gas-phase oxidation of propane to acrolein in an oxidation reactor which is fed with a gas mixture comprising, apart from propane and molecular oxygen as oxidant, at most one diluent gas which is essentially inert under the conditions of the heterogeneously catalyzed gas-phase oxidation.

Acrolein is an important intermediate, for example for the preparation of glutaraldehyde, methionine, folic acid and acrylic acid.

It has long been known that acrolein can be produced industrially by heterogeneously catalyzed gas-phase oxidation of propylene with molecular oxygen over catalysts present in the solid state (cf., for example, DE-A 19 62 431, DE-A 29 43 707, DE-C 1 205 502, EP-A 257 565, EP-A 253 409, U.S. Pat. No. 2,941,007 etc.).

A disadvantage of this procedure is that propylene is a relatively expensive starting material.

EP-A 117 146 discloses the production of acrolein from propane by first partially dehydrogenating propane in the absence of oxygen over suitable catalysts and subsequently converting the propylene present in the resulting product mixture, without prior separation, into acrolein by the abovementioned heterogeneously catalyzed gas-phase oxidation. A disadvantage of this procedure is the necessity for a separate dehydrogenation stage.

It is now generally known that acrolein can be produced directly by heterogeneously catalyzed gas-phase oxidation of propane with molecular oxygen (cf., for example, U.S. Pat. No. 4,472,314; Wm. Curtis Conner Jr. und Stuart Soled, "Propane Oxidation over Mixed Metal Oxides", pp. 1224–38 in Stud. Surf. Sci. Catal., 7 (1981); U.S. Pat. No. 4,302,610; J. Barrault and L. Magaud, "Selective oxidation of propane in the presence of bismuth-based catalysts", pp. 305–14 in Stud. Surf. Sci. Catal. 81 (1994); Ikuya Matsuura and Naomasa Kimura, "Oxidation and ammoxidation of propane over tetragonal type $M^{5+}OPO_4$ catalysts", pp. 271–79 in Stud. Surf. Sci. Catal. 82 45 (1994); Wu Tong-Hao et.al. in Journal of Natural Gas Chemistry, 1 (1994) pp. 53–60; JP-A 6-199 731; Kim, Y. C. et al., Applied Catalysis, 70 (1991), pp. 175–87; Kim, Y. C. et al., Chemistry Letters, 4 (1989) pp. 531–34; JP-A-2-83348; Takita Y. et al., Chemistry Letters, 10 (1989) pp. 1733–36; Kim, Y. C. et al., J. Chem. Soc., Chem. Commun. (1989) pp. 652–53; Kim, Y. C. et al., Catalytic Science and Technology, Vol. 1, Kodanska Ltd. (1991) pp. 439–40; Takita Y. et al., Catalysis Today, 13 (1992) pp. 673–78; Y. Moro-oka, Stud. Surf. Sci. Catal. 75c (1993) pp. 1983–86; U.S. Pat. No. 4,260,822, GB-1340891 and U.S. Pat. No. 3,293,290). The catalysts to be used for this purpose are oxide compositions present in the solid state. The catalytically active oxide composition can contain, in addition to oxygen, only one other element or more than one other element (multimetal oxide compositions). Catalytically active oxide compositions are particularly frequently ones comprising more than one metallic element, in particular transition metal. These multielement oxide compositions are usually not simple physical mixtures of oxides of the elemental constituents, but heterogeneous mixtures of complex polycompounds of these elements.

Catalysts which have been found to be particularly suitable for the gas-phase catalytic oxidation of propane to acrolein are multimetal oxide compositions of the general formula I $$MO_a Bi_b P_c X^1_d X^2_e X^3_f X^4_g O_h \qquad (I),$$

where $X^1$ = V, Nb, Ta, Cr, W, Ga, Ce and/or La, $X^2$ = Li, Na, K, Rb, Cs, Cu, Ag, Au, Pd and/or Pt, $X^3$ = Sn, Pb, Sb, Bi, Te, Fe, Co and/or Ni, $X^4$ = Si, Al, Ti and/or Zr, $a = 0 - 2,$ with the proviso that the sum of
$d = 0 - 2,$ a and d is at least 0.20;

$b = 0 - 1.5,$ with the proviso that the sum of
$c = 0 - 10,$ b and c is at least 0.1;

$e = 0 - 0.5,$ $f = 0 - 0.5,$ $g = 0 - 20$ and $h$ = a number different from zero which is determined by the valence and frequency of the elements different from oxygen in I.

Owing to the fact that propane reacts more sluggishly than does propylene, the heterogeneously catalyzed gas-phase oxidation of propane to acrolein is carried out at a comparatively high temperature, typically at from 350 to 650° C. Since the gas-phase partial oxidation of the propane proceeds exothermically, it is advantageous to carry it out industrially in, for example, fluidized catalyst bed reactors or in multitube fixed-bed reactors in which a heat transfer medium (eg. salt bath or metal melt) is passed through the space surrounding the tubes. The working pressure (absolute pressure) in this industrial heterogeneously catalyzed gas-phase partial oxidation of propane can be below 1 atm, at 1 atm or above 1 atm. It is generally from 1 to 2 atm, but can also be up to 10 atm. The target reaction occurs during the residence time of the reaction mixture in the catalyst charge through which it is passed.

In the industrial heterogeneously catalyzed gas-phase partial oxidation of propane with molecular oxygen there is particular interest, on the one hand, in a high space-time yield of the desired target compound acrolein. Owing to the fact that propane reacts more sluggishly than does propylene, it has therefore often been recommended in the prior art that the gas-phase catalytic partial oxidation of propane, unlike the gas-phase catalytic partial oxidation of propylene, be carried out using a reaction gas starting mixture containing an excess of propane over the other reactant, the molecular oxygen. On the other hand, this partial oxidation of propane has a pronounced exothermic character because of which it is recommended in the prior art, in respect of the industrial gas-phase catalytic oxidative reaction of propane to give acrolein, that either an upper limit be placed on the proportion by volume of propane in the reaction gas starting mixture or the reactants be diluted with a gas which is essentially inert under the conditions of the gas-phase catalytic partial oxidation of propane. A diluent gas which is essentially inert under the conditions of the heterogeneously catalyzed gas-phase partial oxidation is normally considered to be a diluent gas whose constituents remain unaltered, taking each constituent individually, to the extent of at least 97 mol % under the conditions of the heterogeneously catalyzed gas-phase partial oxidation. Examples of such inert diluent gases recommended in the prior art for the industrial gas-phase catalytic partial oxidation of propane are $N_2$, $CO_2$, CO, noble gases and water vapor. A particularly important advantageous effect of the concomitant use of an inert diluent gas is seen in the prior art as being that, at a prescribed oxygen to propane ratio, the addition of an inert diluent gas reduces the explosive tendency of the gas mixture, ie. the addition of an inert diluent gas increases the energy input required for a self-propagating combustion reaction in the gas mixture, which is extremely important for the safety of an industrial procedure. In addition, the prior art attributes an advantageous effect in respect of the selectivity of product formation to the inert diluent gases.

As a result, the prior art describes no industrial catalytic gas-phase partial oxidation of propane with molecular oxygen to give acrolein in which the feed gas mixture (reaction gas starting mixture) comprises more than 70 % by volume of propane.

The above statement also applies, in particular, to EP-A 609 122, EP-A 10902 and also to CN-A 1 105 352, and JP-A 2/83 384 even advises strongly against the use of a propane content of over 60% by volume in the reaction gas starting mixture (the use of a feed gas mixture containing more than 70% by volume of propane is reported in the literature in connection with the catalytic gas-phase oxidation of propane with molecular oxygen to give acrolein only by A. N. Schatalowa and coauthors in Neftechimija 8 (1968), No. 3, pp. 364–369 or the equivalent Russian original document 176878 (published in 1966); however, these publications do not 20 relate to an industrial process for preparing acrolein, but are restricted to laboratory experiments for testing catalysts; in the context of such small-scale experiments, the question of the explosive tendency of the reaction mixture is, however, of surbordinate importance; this is also evidenced by the high reaction temperature of 600° C. employed).

However, a disadvantage of this teaching of the prior art is that for a prescribed catalyst and reaction temperature neither the selectivity of the acrolein formation, nor the conversion of propane achieved in a single pass through the reactor, nor the explosive tendency of the reaction gas starting mixture are fully satisfactory.

It is an object of the present invention to provide an improved industrial process for the heterogeneously catalyzed gas-phase oxidation of propane to acrolein in an oxidation reactor which is fed with a gas mixture comprising, apart from propane and molecular oxygen as oxidant, at most one diluent gas which is essentially inert under the conditions of the heterogeneously catalyzed gas-phase oxidation.

We have found that this object is achieved by a process for the industrial heterogeneously catalyzed gas-phase oxidation of pro- pane to acrolein in an oxidation reactor which is fed with a gas mixture comprising, apart from propane and molecular oxygen as oxidant, at most one diluent gas which is essentially inert under the conditions of the heterogeneously catalyzed gas-phase oxidation, which process is distinguished from the industrial processes of the prior art in that the sluggishly reacting propane itself is used as additional diluent gas so that the reaction gas starting mixture which is fed to the oxidation reactor comprises more than 70% by volume of propane and at least 5% by volume of molecular oxygen. Possible further constituents of the starting mixture for the reaction are the inert diluent gases mentioned above by way of example, viz. $N_2$, $CO_2$, CO, noble gases such as He and/or water vapor.

However, their proportion in the feed gas mixture is preferably low, ie. process variants according to the present invention include those in which the feed gas mixture comprises at least 75% by volume, at least 80% by volume, at least 85% by volume or at least 90–95% by volume of propane. The proportion by volume of molecular oxygen is in all cases at least 5% by volume and can extend to a value which corresponds to 100% by volume minus the proportion by volume of the propane. In the latter case, the gas mixture fed to the oxidation reactor contains no inert diluent gases, ie. the reactant propane is diluted only with itself. Accordingly, reaction gas starting mixtures which are suitable according to the present invention comprise from >70 to 95% by volume of propane, from 5 to <30% by volume of molecular oxygen and from 0 to 25% by volume of inert diluent gases.

Preference is given to reaction gas starting mixtures comprising from 75 to 90% by volume of propane, from 10 to 25% by volume of molecular oxygen and from 0 to 15% by volume of inert diluent gases.

Particular preference is given to reaction gas starting mixtures comprising from 80 (preferably >83.4) to 90% by volume of propane, from 10 to 20% by volume of molecular oxygen and from 0 to 10% by volume of inert diluent gases.

The proportion of inert diluent gases is preferably less than 5% by volume, less than 3% by volume or less than 1% by volume respectively. It is particularly advantageous for the reaction gas starting mixture to contain no inert diluent gases. In this text, an industrial process for the heterogeneously catalyzed gas-phase oxidation of propane to give acrolein with molecular oxygen in an oxidation reactor refers to such a process in which the amount of feed gas mixture passed through the oxidation reactor is at least 500 standard m³/h (standard m³=cubic meters at 1 atm and 25° C.). In general, the above throughput is at least 700 standard m³/h and frequently at least 1,000 or 5,000 standard m³/h. A throughput of 100,000 standard m³/h will normally not be exceeded, ie. typical industrial throughputs are from 10,000 to 60,000 standard m³/h.

Suitable catalysts to be used for the process of the present invention, particularly when using the above reaction gas starting mixtures, are the multimetal oxide compositions of the general formula I as are described in the documents cited above in the discussion of the prior art.

As multimetal oxide compositions to be used according to the present invention, preference is given to those of the general formula II $$Mo_{a'} Bi_{b'} X^5_{c'} X^6_{d'} X^7_{e'} O_{f'} \qquad (II),$$

where $X^5$=V, Nb, Ce, Ta, Fe, Ga and/or P, preferably V, Nb and/or Ce, particularly preferably V and/or Nb, $X^6$=Ag, Li, Na, K, Rb, Cs, Tl, Pd, Pt, Au, Cu, Pb and/or Te, preferably Ag, Li and/or Na, particularly preferably Ag, $X^7$=Si, Al, Ti and/or Zr, a'=0.2–2, b'=0.3–1.5, c'=0–2, preferably 0.2–1, d'=0–0.5, preferably 0.001–0.1, e'=0–20 and f"=a number different from zero which is determined by the valence and frequency of the elements different from oxygen in I, and those of the general formula III $$X^8{}_1P_{a''}X^9{}_{b''}X^{10}{}_{c''}O_{d''}, \quad (III),$$

where
X$^8$=V, Nb, Ta, Cr, Mo and/or W, preferably V, Nb and/or Ta,
X$^9$ =Sn, Sb, Bi, Te, Fe, Co, Ni, Cu, La and/or Ce, preferably Sn, Sb, Bi and/or Te,
X$^{10}$=Li, Na, K, Rb and/or Cs,
a"=1–10,
b"=0–0.5,
c"=0–0.5 and
d"=a number different from zero which is determined by the valence and frequency of the elements different from oxygen in II.

The preparation of these multimetal oxide compositions I to III is known to those skilled in the art and described in the prior art. Typically, suitable sources of the elemental constituents of the multimetal oxide composition are used to produce an intimate dry mixture which is generally calcined at from 450 to 650° C. for some hours. The calcination is most simply carried out in air. Subsequently, the active composition resulting from the calcination is either used as such or is shaped to the desired catalyst geometry in a manner known per se. Naturally, the shaping can also be carried out before calcination. Shaping to the desired catalyst geometry can be achieved, for example, by application to preformed inert catalyst supports where, as already mentioned, the application can be carried out before or after the final calcination. Use can be made here of the customary support materials such as porous or nonporous aluminum oxides, silicon dioxide, thorium dioxide, zirconium dioxide, silicon carbide or silicates such as magnesium or aluminum silicate. The support bodies can have regular or irregular shapes, with regularly shaped support bodies having a distinct surface roughness, eg. spheres or hollow cylinders, being preferred. Suitable supports are essentially nonporous, rough, spherical supports comprising steatite and having a diameter of from 1 to 6 mm, preferably from 4 to 5 mm. The thickness of the layer of active composition is advantageously selected in the range from 50 to 500 μm, preferably in the range from 150 to 250 μm. At this point, it may be remarked that in the production of such coated catalysts the powder composition with which the support bodies are to be coated is generally moistened before application and after application is dried again, eg. by means of hot air.

For producing the coated catalysts, the coating of the support bodies is generally carried out in a suitable rotatable container as is already known, for example, from DE-A 29 09 671 or from EP-A 293 859. The relevant composition is generally calcined before being applied to the support.

Of course, the multimetal oxide compositions according to the present invention can also be used as unsupported catalysts. For this purpose, the intimate dry mixture is preferably compacted directly to give the desired catalyst geometry (eg. by tabletting or extrusion) and calcined. For this shaping step it is possible to add, if desired, auxiliaries customary per se, eg. graphite or stearic acid as lubricant and/or shaping aid and reinforcers such as microfibers of glass, asbestos, silicon carbide or potassium titanate. Here too, calcination can generally also be carried out prior to shaping. One suitable unsupported catalyst geometry is a hollow cylinder having an external diameter and length of from 2 to 10 mm and a wall thickness of from 1 to 3 mm.

As regards the sources of the elemental constituents of the multimetal oxide compositions I to III, it is only important that, as is generally known, they are either oxides or else compounds which can be converted into oxides by heating, at least in the presence of oxygen. Apart from the oxides, other suitable starting compounds are therefore, in particular, halides, nitrates, formates, oxalates, acetates, carbonates or hydroxides. Other suitable starting compounds of Mo, V, W and Nb are their oxo compounds (molybdates, vanadates, tungstates and niobates) or the acids derived from these.

The intimate mixing of the starting compounds for producing multimetal oxide compositions to be used according to the present invention can be carried out dry or wet. If it is carried out dry, the starting compounds are advantageously used as fine powders and after mixing and, if desired, compaction are subjected to calcination. However, the intimate mixing is preferably carried out wet. Here, the starting compounds are usually mixed with one another in the form of an aqueous solution and/or suspension. For example, the drying process can directly follow the preparation of the aqueous mixture and be carried out by spray drying (the outlet temperatures are advantageously from 100 to 150° C.), which gives a particularly intimate dry mixture.

It is important for the purposes of the present invention that the process of the present invention can also be carried out using multimetal oxide compositions I, II and/or III with the exception of those multimetal oxide compositions which are obtainable by intimately mixing dehydrogenating oxides such as magnesium, zinc, aluminum, chromium, copper, potassium and/or iron oxide with an oxidic bismuth molybdate (with or without addition of a small amount of water) and, (if desired after drying) hardening at elevated temperature (eg. about 600° C.).

This means that the process of the present invention can also be successfully carried out using multimetal oxide compositions I, II and/or III with the exception of those multimetal oxide compositions comprising a dehydrogenating metal oxide such as magnesium, zinc, alluminum, chromium, copper, potassium and/or iron oxide as were used in the publications by A. N. Schatalowa stated as prior art.

The reaction temperature employed in the industrial process of the present invention is advantageously from 350 to 650° C. The process of the present invention ensures a particularly high safety standard of temperatures s 550° C., preferably ≦500° C. Since temperatures of <400° C. have a disadvantageous effect on the conversion, the most favorable temperature range according to the present invention is thus from 400 to 550° C., preferably from 400 to 500° C. and particularly preferably from 425 to 475° C.

These statements apply particularly when multimetal oxide compositions of the general formulae I, II and/or III are employed as catalysts.

Of course, the reaction gas starting mixture to be used according to the present invention can be preheated before being fed to the catalyst charge. It is here not disadvantageous if the reaction gas starting mixture is preheated to the desired reaction temperature before being fed to the catalyst charge. For this purpose, a heating apparatus can be provided upstream of the actual oxidation reactor.

If multitube fixed-bed reactors as are described, for example, in the documents DE-A 28 30 765, DE-A 22 01 528 or U.S. Pat. No. 3,147,084 are employed, such an upstream heating apparatus can comprise, as a particularly simple example, a tube section which contains no catalyst and is heated to the reaction temperature. This section can, however, also contain no tubes and can thus correspond to an (individual) tube having a cross section up to that of the reactor. Any partial thermal and/or oxidative dehydrogenation of the propane to give propylene associated with such preheating does not adversely affect the success of the process of the present invention. This also applies when the corresponding decomposition equilibria are established during such preheating.

Multitube fixed-bed reactors suitable for the industrial process of the present invention comprise at least 1,000 individual tubes. In general, they comprise not more than 50,000 individual tubes. A number of at least 5,000 or at least 10,000 individual tubes is typical. The number of tubes accommodated in the reaction vessel is frequently from 15,000 to 30,000. Such multitube fixed-bed reactors correspond in type to shell-and-tube heat exchangers, ie. their simplest type of construction comprises a generally cylindrical vessel in which a plurality of tubes (a tube bundle) corresponding to the cooling tubes of a shell-and-tube heat exchanger is accommodated in a customarily vertical arrangement. Furthermore, heat exchange media are passed through the space surrounding the tubes in order to dissipate the process heat. The tubes are usually made of ferritic steel and typically have a wall thickness of from 1 to 3 mm. Their internal diameter is generally from 20 to 30 mm. The tube length normally extends to a few meters (a tube length in the range from 2 to 4 m is typical). The tubes are normally homogeneously distributed within the reactor.

It is essential to the present invention that, as described in Catalysis Today, 13 (1992), p. 676, the catalyst surface destroys free radicals, which is why the explosive tendency (keyword: free-radical chain reaction) in the process of the present invention is most pronounced in the front end of the catalyst charged. In this respect, it is of particular importance that the use according to the present invention of the reactant propane as diluent surprisingly reduces the explosive tendency of the reaction starting mixture more than does the use of one of the inert diluent gases known per se, viz. $N_2$, CO, $CO_2$, noble gas and/or $H_2O$. Also surprising is the increased selectivity of acrolein formation obtained according to the present invention.

As already mentioned in the introduction, the working pressure in the process of the present invention may extend over a wide range (typically from 0.5 atm to 10 atm). The working pressure is advantageously from 1 to 3 atm, preferably from 1 to 2 atm. When multitube fixed-bed reactors are used, the total space velocity in the process of the present invention is generally set to values of from 200 to 3500 standard 1/l/h.

The acrolein formed can be separated in a manner known per se from the product gas mixture obtainable according to the present invention. Unreacted propane and any propylene formed can be recirculated to the oxidation stage (continuous procedure) and/or used further elsewhere (eg. combustion in thermal power stations to produce energy, synthesis gas or acetylene, etc.). In the case of recirculation to the oxidation stage, inert diluent gases such as $CO_2$, CO, $H_2O$, etc. formed as by-products in the oxidation stage are generally at least partially removed so that the composition of the reaction gas starting mixture remains as required according to the present invention.

Another possible further use of the product gas mixture resulting from the process of the present invention is the catalytic gas-phase oxidation known per se of the acrolein present therein to give acrylic acid. For this purpose, the product gas mixture obtained according to the present invention can most simply be fed as such into an appropriate downstream gas-phase oxidation stage.

It is advantageous according to the present invention that the unreacted propane present in the product gas mixture likewise acts as diluent gas to lower the explosive tendency in such a subsequent gas-phase oxidation stage and increases the process safety in this region too. The simplest apparatus for carrying out this second oxidation stage is formed by an extension of the catalyst bed of the first oxidation stage. Another simple apparatus for carrying out the two oxidation stages is formed by a tube bundle reactor within which the catalyst charge changes appropriately along the individual tubes after the end of the first reaction step. However, the two oxidation stages can also be carried out in two oxidation reactors connected in series (for the acrylic acid stage, appropriate tube bundle reactors can be used, as described for the acrolein stage; they are known in the prior art; cf., for example, DE-A 4 431 949 and literature cited therein;). In this case, the other reaction conditions, eg. the reaction temperature, can also be optimally matched in a simple manner. Advantageously, the molecular oxygen required in this case for the second oxidation stage is fed only to the second oxidation reactor. The amount of oxygen additionally fed in is preferably selected such that the feed gas mixture for the acrylic acid stage comprises an amount of $O_2$ which is from at least stoichiometric to about three times stoichiometric. The safety of the second oxidation stage (acrylic acid stage) can be additionally increased by removing water vapor and $CO_2$ formed as by-products in the first oxidation stage from the product gas mixture leaving the first oxidation stage before it is transferred to the acrylic acid stage. Of course, it is also possible in this respect to separate the acrolein present either completely or at least from part of the other gas components (eg. CO, $CO_2$, $H_2O$, $N_2$) present in the product mixture before the latter is fed to the second oxidation stage. It is self evident that the product gas mixture can have its composition altered as desired by external addition of gaseous components (eg. water vapor) before such further use for preparing acrylic acid. Propane and/or acrolein still present in the product gas mixture from such a downstream acrylic acid stage can likewise be separated off and recirculated to the acrolein and/or acrylic acid stage and/or passed to anaother use elsewhere (eg. combustion in thermal power stations to produce energy, preparation of synthesis gas or acetylene, etc.).

The reaction temperature in such a downstream acrylic acid stage is advantageously from 200 to 350° C., preferably from 230 to 330° C. (an appropriate heat exchanger is advantageously installed between the two oxidation stages). The multimetal oxide catalysts employed in such an acrylic acid stage are the multimetal oxides comprising Mo and V as main constituents to be employed in a manner known per se. Such suitable multimetal oxide catalysts are described, for example, in U.S. Pat. No. 3,775,474, U.S. Pat. No. 3,954,855, U.S. Pat. No. 3,893,951 and U.S. Pat. No. 4,339,355. The multimetal oxide compositions of EP-A 427 508, DE-A 2 909 671, DE-C 3 151 805, DE-B 2 626 887 and DE-A 4 302 991 are also particularly suitable.

Many of the multimetal oxide catalysts suitable for the acrylic acid stage can be described by the general formula IV $$Mo_{12}V_{a'''}W_{b'''}Cu_{c'''}Ni_{d'''}X^{11}_{e'''}X^{12}_{f'''}X^{13}_{g'''}X^{14}_{h'''}X^{15}_{i'''}O_{n'''} \quad (IV),$$

where the variables have the following meanings:
$X^{11}$ is one or more alkali metals,
$X^{12}$ is one or more alkaline earth metals,
$X^{13}$ is chromium, manganese, cerium and/or niobium,
$X^{14}$ is antimony and/or bismuth,
$C^{15}$ is silicon, aluminum, titanium and/or zirconium,
a''' is from 1 to 6,
b''' is from 0.2 to 4,
c''' is from 0.5 to 6,
d''' is from 0.2 to 6,
e''' is from 0 to 2,
f''' is from 0 to 3,
g''' is from 0 to 5,
h''' is from 0 to 40,
i''' is from 0 to 40 and
n''' is a number which is determined by the valence and frequency of the elements different from oxygen.

They are obtainable in a manner known per se (see, for example, DE-A 4 302 991) and are customarily used in unsupported form shaped into spheres, rings or cylinders or else are used in the form of coated catalysts, ie. preshaped inert support bodies coated with the active composition. Of course they can also be employed as catalysts in powder form.

The source of the molecular oxygen required as oxidant in the process of the present invention can be, for example, air. However, since molecular oxygen occurs in air only in association with the inert gas $N_2$ and it is advantageous according to the present invention to work without the presence of inert gases in the reaction gas mixture, the oxygen required for the process of the present invention is normally taken from a pure oxygen source.

In the present document, conversion and selectivity are, unless otherwise indicated, defined as follows:

$$\text{Conversion } C \text{ of propane on a single pass (mol-\%)} = \frac{\text{Number of mol of propane reacted}}{\text{Number of mol of propane used}} \times 100;$$

$$\text{Selectivity } S \text{ of acrolein formation on a single pass (mol-\%)} = \frac{\text{Number of mol of propane reacted to form acrolein}}{\text{Total number of mol of propane reacted}} \times 100;$$

EXAMPLES

A) Preparation of Multimetal Oxide Compositions MI to MIII to be used as Catalysts According to the Present Invention MI: 413.3 g of bismuth nitrate pentahydrate (Bi(NO$_3$)$_3$·5H$_2$O, from Merck, Darmstadt) were dissolved in 400 ml of water at 25° C. and acidified with 40 ml of concentrated nitric acid (65 % strength by weight aqueous solution) to give an aqueous solution A.

In addition, first 79.31 g of ammonium heptamolybdate tetrahydrate (81.7 % by weight of MoO$_3$) and then 65.29 g of ammonium metavanadate (75.2 % by weight of V$_2$O$_5$) were dissolved in 800 ml of water at 95° C. The resulting solution was cooled to 80° C. and 47 ml of a 25% strength by weight aqueous NH$_3$ solution were then added to give an aqueous solution B having a pH of 10. Furthermore, 1.7 g of silver nitrate were dissolved in 5 ml of water to given an aqueous solution C.

The aqueous solutions A and C were then introduced in the specified order (while maintaining the temperature at 80° C.) into the aqueous solution B at 80° C. while stirring vigorously, the resulting aqueous suspension was stirred for 1 hour while maintaining the temperature at 80° C. and subsequently evaporated slowly on a water bath at 80° C. while stirring at atmospheric pressure until a slurry-like consistency was reached. The resulting mass was then dried for 16 hours at 120° C. and 1 atm and finally broken up into catalyst pecursor particles having a number average maximum diameter of 5 mm. The latter were finally calcined for 6 hours at 520° C. in air and milled to give active composition particles having a number average diameter of 150 μm.

The stoichiometry of the active composition particles was:

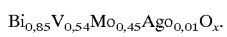

$Bi_{0.85}V_{0.54}Mo_{0.45}Ag_{0.01}O_x$.

MII: 181.9 g of vanadium pentoxide (V$_2$O$_5$, >99% by weight from Merck, Darmstadt) were introduced while stirring into a mixture of 850 ml of water and 230.5 g of 85% strength by weight aqueous phosphoric acid (H$_3$PO$_4$). The resulting aqueous suspension was refluxed for 5 hours at 100° C. at atmospheric pressure while stirring and subsequently evaporated at atmospheric pressure on a water bath at 80° C. until a slurry-like consistency was reached. The resulting mass was dried at 120° C. at atmospheric pressure for 16 hours and finally broken up into catalyst precursor particles having a number average maximum diameter of 5 mm. The latter were finally calcined for 3 hours at 500° C. in air and crushed to give active composition particles having a number average maximum diameter of from 1 to 2 mm.

The stoichiometry of the active composition particles was: VOPO$_4$.

MIII: 500 g of H$_3$PMo$_{12}$O$_{40}$-hydrate (50% by weight of Mo, from Merck, Darmstadt) were dissolved in 1000 ml of water at 25° C. 3270.6 g of an aqueous Bi(NO$_3$)$_3$ solution (11.1% by weight of Bi, acidified to pH=0.3 with HNO$_3$) were added dropwise over a period of 15 minutes while stirring to the first solution. The resulting aqueous suspension was evaporated at atmospheric pressure on a water bath at 70° C. while stirring until a slurry-like consistency was reached. The mass thus obtained was then dried for 16 hours at 120° C. and atmospheric pressure and finally broken up into catalyst precursor particles having a number average maximum diameter of from 5 to 6 mm. These were calcined in air, first for 4.5 hours at 460° C. and then for 2 hours at 520° C., and crushed to give active composition particles having a number average diameter of from 1 to 2 mm.

The stoichiometry of the active composition particles was: Bi$_8$PMo$_{12}$O$_x$.

B) Catalytic Gas-Phase Oxidation of Propane using the Multimetal Oxide Compositions MI to MIII as Catalysts E1: In a V2A steel reaction tube having an internal diameter of 17 mm (wall thickness: 2 mm), a length of 25 cm and fitted with a thermocouple sheath having an external diameter of 3 mm running centrally along the entire tube, an active composition charge comprising 2 g of the active composition particles MI and 10 g of steatite spheres (2 mm diameter, for diluting the active composition) was placed on a fine support mesh of V2A steel which closed off the reaction tube. The reaction tube itself was surrounded along its entire length by a salt bath at 450° C. 6 standard l/h of reaction gas starting mixture at 25° C. was fed into the reaction tube from the opposite end to the support mesh. The product gas mixture leaving the tube was analyzed on-line by gas chromatography.

Depending on the composition Z of the reaction gas starting mixture, the following results were obtained:

| Z | | | | |
|---|---|---|---|---|
| $N_2$ (% by volume) | Propane (% by volume) | $O_2$ (% by volume) | $CO_2$ (% by volume) | S (acrolein, mol %) |
| — | 33 | 67 | — | 5 |
| — | 50 | 50 | — | 6 |
| — | 75 | 25 | — | 8 |
| — | 80 | 20 | — | 9 |
| 10 | 45 | 45 | — | 8 |
| — | 45 | 45 | 10 | 8 |

It is surprising that the selectivity of acrolein formation increases with an increasing proportion of propane in the feed gas mixture.

E2: As E1, but the active composition charge comprised a mixture of 4 g of the active composition particles MII and 20 g of the steatite spheres. In addition, the feed rate of the propane/$O_2$ reaction gas starting mixture was 20 standard l/h and the salt bath temperature was 480° C.

The results obtained are:

| Z | | |
|---|---|---|
| Propane (% by volume) | $O_2$ (% by volume) | S (acrolein, mol %) |
| 67 | 33 | 6 |
| 80 | 20 | 9 |

E3: As E1, but the active composition charge consisted exclusively of 4 g of the active composition particles III.

The results achieved are:

| Z | | |
|---|---|---|
| Propane (% by volume) | $O_2$ (% by volume) | S (acrolein, mol %) |
| 67 | 33 | 5 |
| 80 | 20 | 8 |

C) Examination of the Explosive Tendency of Various Reaction Gas Starting Mixtures The experiments were carried out in a closed, spherical 5 l high-pressure vessel made of stainless steel. The gas mixture was made up in the initially evacuated high-pressure vessel by means of the partial pressure method. After a mixing time of 10 min by means of a magnetic stirrer, an attempt was made to ignite the gas mixture (in each case at a pressure of 2 atm and an initial temperature T) by means of a platinum wire heated to melting.

Any self-propagating reaction front (explosion) triggered in this way was detected by means of the rise over time of the internal pressure in the vessel (measured using a piezo-electric pressure sensor) and by means of the increase in the temperature in the vessel.

The following results were obtained
(+: explosion; −: no explosion)

| | Composition of gas mixture | Initial temperature T | Explosion? |
|---|---|---|---|
| a) | 59% by volume of propane 41% by volume of $O_2$ | ≦20° C. | − |
| b) | 59% by volume of propane 41% by volume of $O_2$ | >20° C. | + |
| c) | 61.5% by volume of propane 38.5% by volume of $O_2$ | ≦120° C. | − |
| d) | 61.5% by volume of propane 38.5% by volume of $O_2$ | >120° C. | + |
| e) | 59.0% by volume of propane 38.5% by volume of $O_2$ 2.5% by volume of $N_2$ | ≦41° C. | − |
| f) | 59.0% by volume of propane 38.5% by volume of $O_2$ 2.5% by volume of $N_2$ | >41° C. | + |
| g) | 59.0% by volume of propane 38.5% by volume of $O_2$ 2.5% by volume of $CO_2$ | ≦50° C. | − |
| h) | 59.0% by volume of propane 38.5% by volume of $O_2$ 2.5% by volume of $CO_2$ | >50° C. | + |
| i) | 59.0% by volume of propane 38.5% by volume of $O_2$ 2.5% by volume of He | ≦10° C. | − |
| j) | 59.0% by volume of propane 38.5% by volume of $O_2$ 2.5% by volume of He | >10° C. | + |
| k) | 65.5% by volume of propane 34.5% by volume of $O_2$ | ≦220° C. | − |
| l) | 65.5% by volume of propane 34.5% by volume of $O_2$ | >220° C. | + |
| m) | 67.5% by volume of propane 32.5% by volume of $O_2$ | ≦260° C. | − |
| n) | 67.5% by volume of propane 32.5% by volume of $O_2$ | >260° C. | + |
| o) | 65.5% by volume of propane 32.5% by volume of $O_2$ 2.0% by volume of $N_2$ | ≦220° C. | − |
| p) | 65.5% by volume of propane 32.5% by volume of $O_2$ 2.0% by volume of $N_2$ | >220° C. | + |

The results demonstrate that, starting from a particular gas mixture consisting of only molecular oxygen and propane (having a proportion of propane of at least about 60% by volume), addition of propane has a significantly greater effect in reducing the explosive tendency of the gas mixture than does an addition of an inert diluent gas.

In summary, the above examples thus demonstrate without doubt that for the industrial heterogeneously catalyzed gas-phase oxidation of propane with molecular oxygen, the reactant propane is surprisingly by far the most favorable diluent gas.

We claim:
1. A process for the industrial heterogeneously catalyzed gasphase oxidation of propane to acrolein, comprising:
   feeding a gas mixture comprising propane molecular oxygen as oxidant, and at most one inert diluent gas to an oxidation reactor containing a catalyst;
   wherein said gas mixture comprises more than 70% by volume of propane and at least 5% by volume of molecular oxygen per 100% by volume of said gas mixture, wherein said catalyst is a multimetal oxide composition of formula (I)

wherein
X$^1$=V, Nb, Ta, Cr, W, Ga, Ce and/or La,
X$^2$=Li, Na, K, Rb, CS, Cu, Ag, Au, Pd and/or Pt,
X$^3$=Sn, Pb, Sb, Bi, Te, Fe, Co and/or Ni,
X$^4$=Si, Al, Ti and/or Zr,
a=0–2,
d=0–2, with the proviso that the sum of a and d is at least 0.20;
b=0–1.5,
c=0–10, with the proviso that the sum of b and c is at least 0.1;
e=0–0.5,
f=0–0.5,
g=0–20 and
h=a number different from zero which is determined by the valence and frequency of the elements different from oxygen in (I);
wherein said catalyst is an unsupported catalyst having a geometry of a hollow cylinder;
wherein an external diameter and a length of said hollow cylinder are from 2 to 10 mm; and
wherein a wall thickness of said hollow cylinder is from 1 to 3 mm.

2. A process as claimed in claim 1, wherein said gas mixture comprises at least 75% by volume of propane per 100% by volume of said gas mixture.

3. A process as claimed in claim 1, wherein said gas mixture comprises at least 80% by volume of propane per 100% by volume of said gas mixture.

4. A process as claimed in claim 1, wherein said gas mixture comprises at least 85% by volume of propane per 100% by volume of said gas mixture.

5. A process as claimed in claim 1, wherein said gas mixture comprises at least 90% by volume of propane per 100% by volume of said gas mixture.

6. A process as claimed in claim 1, wherein said gas mixture comprises 95% by volume of propane per 100% by volume of said gas mixture.

7. A process as claimed in claim 1, wherein said gas mixture comprises at least 10% by volume of molecular oxygen per 100% by volume of said gas mixture.

8. A process as claimed in claim 1, wherein said gas mixture comprises at least 15% by volume of molecular oxygen per 100% by volume of said gas mixture.

9. A process as claimed in claim 1, wherein said gas mixture comprises at least 20% by volume of molecular oxygen per 100% by volume of said gas mixture.

10. A process as claimed in claim 1, wherein said gas mixture comprises at least 25% by volume of molecular oxygen per 100% by volume of said gas mixture.

11. A process as claimed in claim 1, wherein said gas mixture comprises <30% by volume of molecular oxygen per 100% by volume of said gas mixture.

12. A process as claimed in claim 1, wherein said inert diluent gas is N$_2$, CO, CO$_2$, a nobel gas, water vapor or mixtures thereof.

13. A process as claimed in claim 1, wherein a working pressure is from 0.5 to 10 atm.

14. A process as claimed in claim 13, wherein said working pressure is from 1 to 3 atm.

15. A process as claimed in claim 13, wherein said working pressure is from 1 to 2 atm.

16. A process as claimed in claim 1, wherein said process is carried out in a fluidized catalyst bed.

17. A process as claimed in claim 1, wherein said process is carried out in a multitude fixed-bed reactor.

18. A process as claimed in claim 1, wherein said process is carried out at a temperature of 350 to 650° C.

19. A process as claimed in claim 18, wherein said process is carried out at a temperature of 400 to 550° C.

20. A process as claimed in claim 18, wherein said process is carried out at a temperature of 425 to 475° C.

21. A process as claimed in claim 1, wherein said gas mixture is preheated to a reaction temperature before being fed to a catalyst charge.

22. A process as claimed in claim 1, wherein said process is carried out continuously, with unreacted propane and/or propene present in a product gas mixture being separated off and returned to said gas phase oxidation.

23. An industrial process for preparing acrylic acid, wherein an acrolein-containing product gas mixture is first produced by a process as claimed in claim 1 and said acrolein present in said product gas mixture is subsequently further oxidized in a second oxidation stage to give acrylic acid.

24. A process as claimed in claim 23, wherein said acrolein-containing product gas mixture is fed to said second oxidation stage without prior removal of substances.

25. A process as claimed in claim 24, wherein said process is carried out continuously, with unreacted propane and/or acrolein present in the acrylic acid-containing product gas mixture being separated off and returned to said gas-phase oxidation and/or passed to another use elsewhere.

26. A process for the industrial heterogeneously catalyzed gasphase oxidation of propane to acrolein, comprising:
feeding a gas mixture comprising propane, molecular oxygen as oxidant and at most one inert diluent gas to an oxidation reactor containing a catalyst;
wherein said gas mixture comprises more than 70% by volume of propane and at least 5% by volume of molecular oxygen per 100% by volume of said gas mixture,
wherein said catalyst is a multimetal oxide composition of formula (II)

wherein
X$^5$=V, Nb, Ce, Ta, Fe, Ga and/or P,
X$^6$=Ag, Li, Na, K, Rb, Cs, TI, Pd, Pt, Au, Cu, Pb and/or Te,
X$^7$=Si, Al, Ti and/or Zr,
a'=0.2–2
b'=0.3–1.5,
c'=0–2,
d'=0–0.5
e'=0–20 and
f'=a number different from zero which is determined by the valence and frequency of the elements different from oxygen in (II);
wherein said catalyst is an unsupported catalyst having a geometry of a hollow cylinder;

wherein an external diameter and a length of said hollow cylinder are from 2 to 10 mm; and wherein a wall thickness of said hollow cylinder is from 1 to 3 mm.

27. A process as claimed in claim 26, wherein $X^5$=V, Nb and/or Ce.

28. A process as claimed in claim 26, wherein $X^5$=V, Nb or a mixture thereof.

29. A process as claimed in claim 26, wherein $X^6$ Ag, Li and/or Na.

30. A process as claimed in claim 26, wherein c'=0.2–1.

31. A process as claimed in claim 26, wherein d'=0.001–0.1.

32. A process as claimed in claim 26, wherein said gas mixture comprises at least 75% by volume of propane per 100% by volume of said gas mixture.

33. A process as claimed in claim 26, wherein said gas mixture comprises at least 80% by volume of propane per 100% by volume of said gas mixture.

34. A process as claimed in claim 26, wherein said gas mixture comprises at least 85% by volume of propane per 100% by volume of said gas mixture.

35. A process as claimed in claim 26, wherein said gas mixture comprises at least 90% by volume of propane per 100% by volume of said gas mixture.

36. A process as claimed in claim 26, wherein said gas mixture comprises 95% by volume of propane per 100% by volume of said gas mixture.

37. A process as claimed in claim 26, wherein said gas mixture comprises at least 0% by volume of molecular oxygen per 100% by volume of said gas mixture.

38. A process as claimed in claim 26, wherein said gas mixture comprises at least 15% by volume of molecular oxygen per 100% by volume of said gas mixture.

39. A process as claimed in claim 26, wherein said gas mixture comprises at least 20% by volume of molecular oxygen per 100% by volume of said gas mixture.

40. A process as claimed in claim 26, wherein said gas mixture comprises at least 25% by volume of molecular oxygen per 100% by volume of said gas mixture.

41. A process as claimed in claim 26, wherein said gas mixture comprises <30% by volume of molecular oxygen per 100% by volume of said gas mixture.

42. A process as claimed in claim 26, wherein said inert diluent gas is $N_2$, CO, $CO_2$, a nobel gas, water vapor and mixtures thereof.

43. A process as claimed in claim 26, wherein a working pressure is from 0.5 to 10 atm.

44. A process as claimed in claim 43, wherein said working pressure is from 1 to 3 atm.

45. A process as claimed in claim 43, wherein said working pressure is from 1 to 2 atm.

46. A process as claimed in claim 26, wherein said process is carried out in a fluidized catalyst bed.

47. A process as claimed in claim 26, wherein said process is carried out in a multitude fixed-bed reactor.

48. A process as claimed in claim 26, wherein said process is carried out at a temperature of 350 to 650° C.

49. A process as claimed in claim 48, wherein said process is carried out at a temperature of 400 to 550° C.

50. A process as claimed in claim 48, wherein said process is carried out at a temperature of 425 to 475° C.

51. A process as claimed in claim 26, wherein said gas mixture is preheated to a reaction temperature before being fed to a catalyst charge.

52. A process as claimed in claim 26, wherein said process is carried out continuously, with unreacted propane and/or propene present in a product gas mixture being separated off and returned to said gas phase oxidation.

53. An industrial process for preparing acrylic acid, wherein an acrolein-containing product gas mixture is first produced by a process as claimed in claim 26 and said acrolein present in said product gas mixture is subsequently further oxidized in a second oxidation stage to give acrylic acid.

54. A process as claimed in claim 53, wherein said acrolein-containing product gas mixture is fed to said second oxidation stage without prior removal of substances.

55. A process as claimed in claim 54, wherein said process is carried out continuously, with unreacted propane and/or acrolein present in the acrylic acid-containing product gas mixture being separated off and returned to said gas-phase oxidation and/or passed to another use elsewhere.

56. A process for the industrial heterogeneously catalyzed gasphase oxidation of propane to acrolein, comprising:

feeding a gas mixture comprising propane, molecular oxygen as oxidant, and at most one inert diluent gas to an oxidation reactor containing a catalyst;

wherein said gas mixture comprises more than 70% by volume of propane and at least 5% by volume of molecular oxygen per 100% by volume of said gas mixture;

wherein said catalyst is a multimetal oxide composition of formula (III)

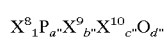

wherein $X^8$=V, Nb, Ta, Cr, Mo and/or W, $X^9$=Sn, Sb, Si, Te, Fe, Co, Ni, Cu, La and/or Ce, $X^{10}$=Li, Na, K, Rb and/or Cs, a"=1–10, b"=0–0.5, c"=0–0.5 and d"–a number different from zero which is determined by the valence and frequency of the elements different from oxygen in (III), wherein said catalyst is an unsupported catalyst having a geometry of a hollow cylinder;

wherein an external diameter and a length of said hollow cylinder are from 2 to 10 mm; and wherein a wall thickness of said hollow cylinder is from 1 to 3 mm.

57. A process as claimed in claim 56, wherein said gas mixture comprises at least 75% by volume of propane per 100% by volume of said gas mixture.

58. A process as claimed in claim 56, wherein said gas mixture comprises at least 80% by volume of propane per 100% by volume of said gas mixture.

59. A process as claimed in claim 56, wherein said gas mixture comprises at least 85% by volume of propane per 100% by volume of said gas mixture.

60. A process as claimed in claim 56, wherein said gas mixture comprises at least 90% by volume of propane per 100% by volume of said gas mixture.

61. A process as claimed in claim 56, wherein said gas mixture comprises 95% by volume of propane per 100% by volume of said gas mixture.

62. A process as claimed in claim 56, wherein said gas mixture comprises at least 10% by volume of molecular oxygen per 100% by volume of said gas mixture.

63. A process as claimed in claim 56, wherein said gas mixture comprises at least 15% by volume of molecular oxygen per 100% by volume of said gas mixture.

64. A process as claimed in claim 56, wherein said gas mixture comprises at least 20% by volume of molecular oxygen per 100% by volume of said gas mixture.

65. A process as claimed in claim 56, wherein said gas mixture comprises at least 25% by volume of molecular oxygen per 100% by volume of said gas mixture.

66. A process as claimed in claim 56, wherein said gas mixture comprises <30% by volume of molecular oxygen per 100% by volume of said gas mixture.

67. A process as claimed in claim 56, wherein said inert diluent gas is $N_2$, CO, $CO_2$, a nobel gas, water vapor, and mixture thereof.

68. A process as claimed in claim 56, wherein $X^8$=V, Nb and/or Ta.

69. A process as claimed in claim 56, wherein $X^9$=S, Sb, Bi and/or Te.

70. A process as claimed in claim 56, wherein a working pressure is from 0.5 to 10 atm.

71. A process as claimed in claim 70, wherein said working pressure is from 1 to 3 atm.

72. A process as claimed in claim 70, wherein said working pressure is from 1 to 2 atm.

73. A process as claimed in claim 56, wherein said process is carried out in a fluidized catalyst bed.

74. A process as claimed in claim 56, wherein said process is carried out in a multitude fixed-bed reactor.

75. A process as claimed in claim 56, wherein said process is carried out at a temperature of 350 to 650° C.

76. A process as claimed in claim 75, wherein said process is carried out at a temperature of 400 to 550° C.

77. A process as claimed in claim 75, wherein said process is carried out at a temperature of 425 to 475° C.

78. A process as claimed in claim 56, wherein said gas mixture is preheated to a reaction temperature before being fed to a catalyst charge.

79. A process as claimed in claim 56, wherein said process is carried out continuously, with unreacted propane and/or propene present in a product gas mixture being separated off and returned to said gas-phase oxidation.

80. An industrial process for preparing acrylic acid, wherein an acrolein-containing product gas mixture is first produced by a process as claimed in claim 56 and said acrolein present in said product gas mixture is subsequently further oxidized in a second oxidation stage to give acrylic acid.

81. A process as claimed in claim 80, wherein said acrolein-containing product gas mixture is fed to said second oxidation stage without prior removal of substances.

82. A process as claimed in claim 81, wherein said process is carried out continuously, with unreacted propane and/or acrolein present in the acrylic acid-containing product gas mixture being separated off and returned to said gas-phase oxidation and/or passed to another use elsewhere.

* * * * *